(12) United States Patent
Cage

(10) Patent No.: US 9,237,959 B2
(45) Date of Patent: Jan. 19, 2016

(54) STENT AND BARB

(75) Inventor: Logan M. Cage, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 305 days.

(21) Appl. No.: 12/188,026

(22) Filed: Aug. 7, 2008

(65) Prior Publication Data

US 2009/0048664 A1 Feb. 19, 2009

Related U.S. Application Data

(60) Provisional application No. 60/956,534, filed on Aug. 17, 2007.

(51) Int. Cl.
*A61F 2/82* (2013.01)
*A61F 2/86* (2013.01)
*A61F 2/915* (2013.01)
*A61F 2/848* (2013.01)

(52) U.S. Cl.
CPC . *A61F 2/86* (2013.01); *A61F 2/915* (2013.01); *A61F 2/848* (2013.01); *A61F 2002/8483* (2013.01); *A61F 2220/0016* (2013.01)

(58) Field of Classification Search
CPC .......................................................... A61F 2/82
USPC ...................... 623/1.14, 1.36, 2.17
See application file for complete search history.

(56) References Cited

U.S. PATENT DOCUMENTS

| | | |
|---|---|---|
| 5,151,105 A | 9/1992 | Kwan-Gett |
| 5,375,612 A | 12/1994 | Cottenceau et al. |
| 5,489,295 A | 2/1996 | Piplani et al. |
| 5,720,776 A | 2/1998 | Chuter et al. |
| 5,733,325 A | 3/1998 | Robinson et al. |
| 5,755,777 A | 5/1998 | Chuter |
| 5,782,904 A | 7/1998 | White et al. |
| 5,824,040 A | 10/1998 | Cox et al. |
| 5,860,998 A | 1/1999 | Robinson et al. |
| 5,891,193 A | 4/1999 | Robinson et al. |
| 5,935,161 A | 8/1999 | Robinson et al. |
| 5,961,546 A | 10/1999 | Robinson et al. |
| 6,053,943 A | 4/2000 | Edwin et al. |
| 6,077,297 A | 6/2000 | Robinson et al. |
| 6,152,937 A | 11/2000 | Peterson et al. |
| 6,210,432 B1 | 4/2001 | Solem et al. |
| 6,231,581 B1 | 5/2001 | Shank et al. |
| 6,371,982 B2 | 4/2002 | Berg et al. |
| 6,451,048 B1 | 9/2002 | Berg et al. |
| 6,547,819 B2 | 4/2003 | Strecker |
| 6,849,087 B1 | 2/2005 | Chuter |
| 6,887,266 B2 | 5/2005 | Williams et al. |
| 7,011,679 B2 | 3/2006 | Lauterjung |
| 7,025,791 B2 | 4/2006 | Levine et al. |
| 7,081,132 B2 | 7/2006 | Cook et al. |
| 7,381,219 B2 | 6/2008 | Salahieh et al. |
| 7,591,848 B2 * | 9/2009 | Allen .......................... 623/2.17 |
| 2002/0123790 A1 | 9/2002 | White et al. |
| 2003/0018377 A1 | 1/2003 | Berg et al. |
| 2003/0120331 A1 | 6/2003 | Chobotov et al. |

(Continued)

*Primary Examiner* — Thomas J Sweet
*Assistant Examiner* — Matthew Schall
(74) *Attorney, Agent, or Firm* — Brinks Gilson & Lione

(57) ABSTRACT

A stent is described and comprises an elongate strut having a first end and a second end, an aperture formed in the strut, and a barb having a base and a distal anchor. The barb base is attached to the strut and the barb extends distally from the base through the aperture. Other devices, systems, and methods are described.

27 Claims, 4 Drawing Sheets

(56) References Cited

U.S. PATENT DOCUMENTS

| | | |
|---|---|---|
| 2003/0125797 A1 | 7/2003 | Chobotov et al. |
| 2003/0220683 A1 | 11/2003 | Minasian et al. |
| 2003/0236570 A1 | 12/2003 | Cook et al. |
| 2005/0033398 A1 | 2/2005 | Seguin |
| 2005/0038497 A1 | 2/2005 | Neuendorf et al. |
| 2005/0038506 A1 | 2/2005 | Webler et al. |
| 2005/0125051 A1 | 6/2005 | Eidenschink et al. |
| 2005/0240259 A1 | 10/2005 | Sisken et al. |
| 2006/0069424 A1 | 3/2006 | Acosta et al. |
| 2007/0005129 A1 | 1/2007 | Damm et al. |
| 2008/0269869 A1 | 10/2008 | Cho |

\* cited by examiner

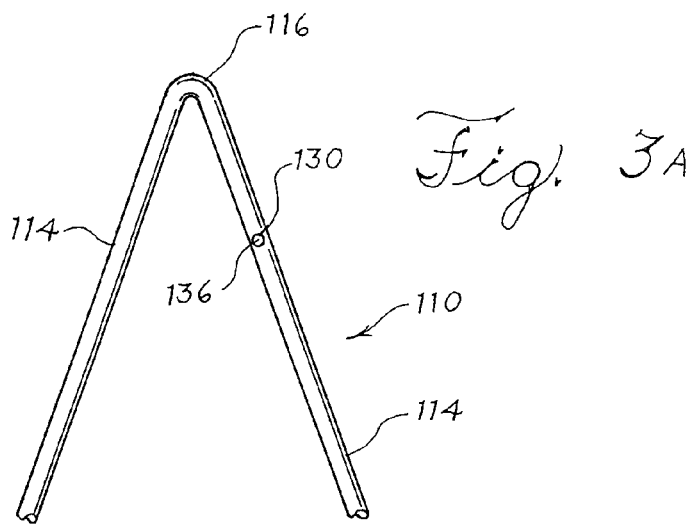
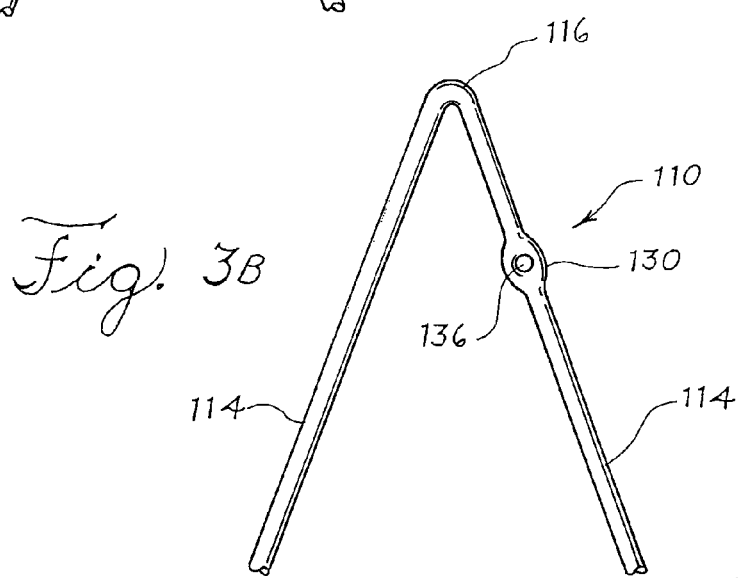
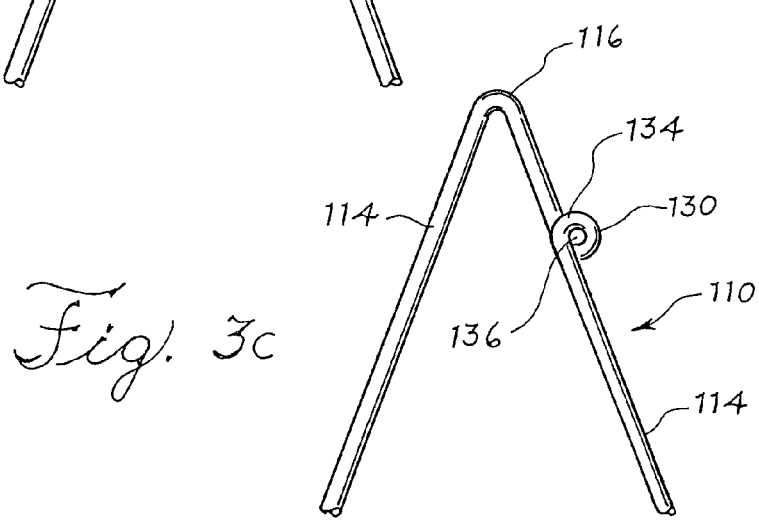

STENT AND BARB

RELATED APPLICATIONS

This patent document claims the benefit of the filing date under 35 U.S.C. §119(e) of U.S. Provisional Patent Application Ser. No. 60/956,534, filed Aug. 17, 2007 which is herein incorporated by reference in its entirety.

BACKGROUND OF THE INVENTION

1. Field of the Invention

This invention relates to medical devices and, in particular, to prostheses for placement in a body lumen.

2. Description of Related Art

The functional vessels of human and animal bodies such as the esophagus, bile duct, and blood vessels occasionally become damaged or diseased. For example, the aortic wall can weaken, resulting in an aneurysm. Upon further exposure to haemodynamic forces, an aneurysm can rupture.

Intraluminal prostheses, such as stents and stent grafts, may be used for treating damaged or diseased functional vessels. For example, a stent graft may be used for repairing abdominal and thoracic aortic aneurysms. Such a stent graft is placed inside the vessel and provides some or all of the functionality of the original, healthy vessel.

One of the challenges of designing and using an intraluminal prosthesis is preventing migration of the prosthesis once it is placed in a body lumen. This challenge is particularly great when the environment in which the prosthesis is placed is subject to a continuous strain, such as by the pulsatile force of blood flow in the vasculature. When an intraluminal prosthesis is used, for example, to repair an aneurysm, migration of the device may result in inadequate exclusion of the aneurysm, and increased risk of aneurysm rupture.

Various devices have been proposed to address migration. For example, a prosthesis may comprise one or more barbs or hooks that extend outwardly from the prosthesis and are configured to engage surrounding body tissue. Typically, such barbs or hooks may be attached to the prosthesis, for example, by sewing, gluing, wrapping, chemical bonding, welding, brazing, soldering, and the like.

Although each of these attachment methods may create a strong bond between the barb and the prosthesis, these bonds have been known to break when the device is placed in situ. One possible explanation is that the attachment is particularly prone to the mechanical and chemical hazards of the intraluminal environment. For example, cardiovascular pulsatile forces may be concentrated at the junction between the barb and the stent, which may also be the site of a weld, solder, or the like. In addition, the saline, oxygen-rich, and acidic physiological environment of the body may tend to weaken and corrode the stent-barb attachment.

One solution to address barb detachment was disclosed in U.S. Pat. No. 5,720,776 to Chuter et al. The barb includes both a mechanical attachment, as well as the traditional solder bond. The mechanical attachment comprises a helical winding of the base of the barb around a strut of the stent. This mechanical attachment supplements the traditional solder bond to help protect the solder joint from breaking. In addition, the barb is made laterally flexible to help accommodate forces acting at the anchor point. These improvements help ensure that the barb does not readily separate from the stent due to a failure of the solder joint alone. While the combination of both solder and a mechanical means to affix the barb to the stent has proved effective in most respects, this area of the barb remains most subject to stresses, such as from cyclic load resulting from the pulsatile action of the implant vessel.

SUMMARY

Various devices, systems, and methods are disclosed throughout the specification and in the drawings. In one example, a stent may be provided and comprise an elongate strut having a first end and a second end, an aperture formed in the strut, and a barb having a base and a distal anchor. The barb base is attached to the strut and the barb extends distally from the base through the aperture.

The aperture may be formed at a strut end or between the first and second ends of the strut. In examples where the stent comprises a first strut and a second strut joined at an apex, the aperture may be formed in the apex.

The aperture may comprise any suitable configuration or structure. In one example, the aperture comprises a winding. In another example, the aperture is forged in the strut. The aperture may define a cavity having any suitable contour. For example, the aperture may comprise a generally cylindrical cavity or a generally frustoconical cavity. Other shapes and contours are contemplated and are within the scope of the present invention. The cavity may extend at an oblique angle or at a generally transverse angle with respect to a longitudinal axis of the strut.

In some examples, the barb base may have a diameter that is less than or equal to the diameter of the aperture. In other examples, the barb base may have a diameter that is greater than a diameter of the aperture. In these cases, it may not be possible to pass the barb base through the aperture. The barb base may be attached to the strut so that it is spaced apart from the aperture along the strut. Alternatively, the barb base may be disposed adjacent the aperture or at least partially within the aperture.

The aperture may have any dimension that is suitable for the particular application. For example, the aperture may have an inner diameter that is less than or equal to 0.030 inches, less than or equal to 0.020 inches, or less than or equal to 0.010 inches.

In another example, a stent may be provided and comprise an elongate strut having a first end and a second end, and a barb having a base and a distal anchor, where the barb base is attached to the strut. The barb base may extend distally from the base and pass through the strut. The stent may comprise one or more additional features as described above.

In another example, a method of attaching a barb to a stent strut comprises the steps of forming an aperture in a strut, passing a barb through the aperture, and fixing the barb to the strut so that at least a portion of the barb is disposed within the aperture. Additional features may be provided as described throughout the specification and figures.

BRIEF DESCRIPTION OF THE DRAWINGS

FIGS. 3A-3E are schematic views of portions of stents and depict apertures of various configurations;

DETAILED DESCRIPTION OF THE PREFERRED EMBODIMENTS

Throughout the specification, when referring to a barb or a portion thereof, the terms "distal" and "distally" shall denote a position, direction, or orientation along the barb that is generally towards or in the direction of the anchor, whereas the terms "proximal" and "proximally" shall denote a position, direction, or orientation along the barb that is generally away from or in the opposite direction of the anchor.

The term "prosthesis" means any device, object, or structure that supports, repairs, or replaces, or is configured to support, repair, or replace a body part or a function of that body part. It can also mean a device that enhances or adds functionality to a physiological system.

The term "stent" means any device or structure that provides or is configured to provide rigidity, expansion force, or support to a body part, for example, a diseased, damaged, or otherwise compromised body lumen. A stent may comprise any suitable material, including, but not limited to, biocompatible metals and plastics. Examples of suitable materials include metals such as stainless steel and NITINOL, and plastics such as polyethylene terephthalate ("PET"), polytetrafluoroethylene ("PTFE") and polyurethane.

A stent may be "expandable," that is, it may be capable of being expanded to a larger-dimension configuration. A stent may be self-expanding and expand by virtue of its own resilience, pressure-expandable and expand only upon the application of an external force, or may have both self-expanding and pressure-expandable features. In one example, a stent may have one or more self-expanding portions and one or more balloon-expandable portions. An example of a suitable self-expanding stent includes Z-STENTS®, which are available from Cook Incorporated, Bloomington, Ind., USA.

The term "lumen" describes a cavity or channel within a tube or a tubular body, such as vessel. The term "intraluminal" means within a lumen, and can refer to objects that are found or that can be placed within a lumen, or methods or processes that occur within a lumen. An "intraluminal prosthesis" is thus a prosthesis that is found or that can be placed within a lumen. Examples of intraluminal prostheses include, but are not limited to, stents, grafts, stent grafts, venous or aortal valves, and vena cava filters. An intraluminal prosthesis may be generally tubular and comprise one or more lumens. Examples of tubular prostheses include straight, branched, and bifurcated prostheses.

Figure 1:
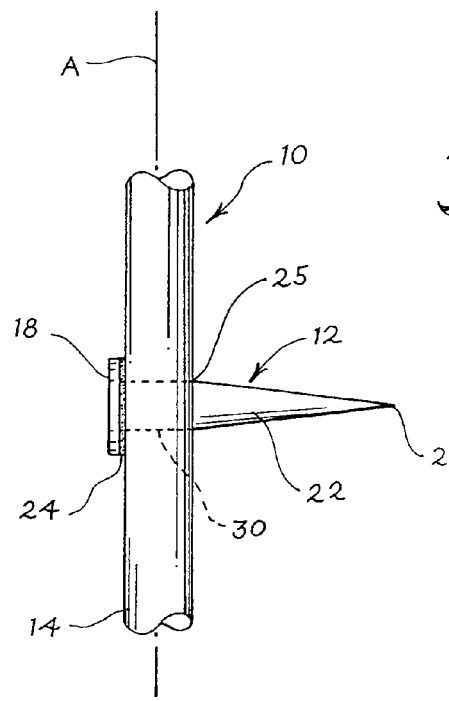
FIG. 1 is a side schematic view of an intraluminal prosthesis comprising a stent and a barb.

FIG. 1 depicts an intraluminal prosthesis comprising a stent 10 and at least one barb 12. The barb 12 comprises a base 18, a distal anchor 20, and a body 22 extending along the barb between the base 18 and the anchor 20. The barb 12 may attach to the prosthesis via the base 18. The anchor 20 is configured to extend outwardly from the prosthesis so that, in use, it may engage tissue and prevent movement between the prosthesis and the vessel in which the prosthesis is placed.

The barb may comprise a suitable biocompatible material, such as a biocompatible metal or plastic. Suitable biocompatible materials include the stent materials described above. Where the stent comprises a metal, the barb 12 and the stent 10 may comprise the same or a similar material. For example, the materials may have similar electromotive forces. Such a construction may minimize corrosion at the junction between the barb and the stent.

Figure 2:
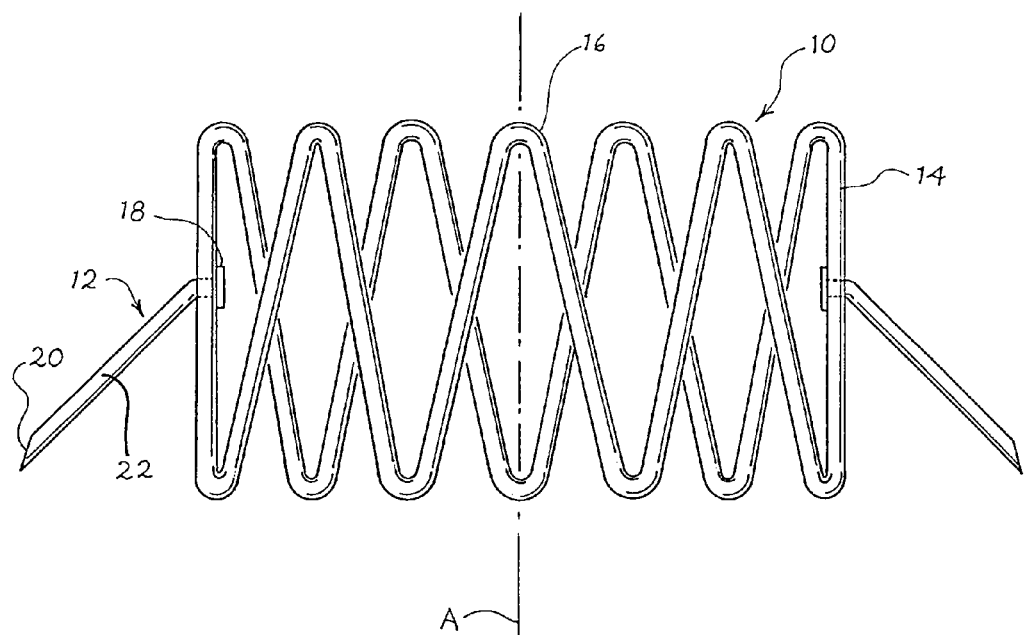
FIG. 2 is a schematic view of a zigzag stent comprising multiple barbs.

As shown in FIGS. 1 and 2, the anchor 20 may extend outwardly from the prosthesis and may be disposed at an angle relative to an axis A of the stent 10. As shown in FIG. 1, the anchor 20 may extend at an angle of approximately 90° to the stent axis A. Alternatively, as shown in FIG. 2, the anchor 20 may extend at an oblique angle, or at an angle that is less than or greater than 90° to the stent axis A.

The stent 10 may comprise at least one strut 14. For example, the stent 10 may comprise a plurality of struts 14 that are arranged in a pattern, such as the alternating zig-zag pattern depicted in FIG. 2. In this example, the struts 14 are joined by one or more apices 16 that define alternating "peaks" and "valleys."

A barb may be secured to a prosthesis by any suitable means known in the art. As shown in FIGS. 1 and 2, the barb 12 may attach to the stent 10 via a fixing element 24, such as a weld, solder, adhesive, or the like. Additionally, or alternatively, a barb 12 may attach to a stent by crimping, wrapping, or otherwise mechanically securing the barb around a strut 14. If the prosthesis includes a graft, the barb 12 may additionally or alternatively attach to the graft, for example by suturing, gluing, interweaving, or the like.

As shown in various examples depicted throughout the specification and in the figures, a barb may be secured to a prosthesis by fitting the barb through a hole or aperture in the strut. FIG. 1 depicts a stent 10 comprising a strut 14 and an aperture 30 formed in the strut. At least a portion of the barb 12 is disposed within a cavity defined by the aperture 30. The barb 12 may engage the cavity and, in some examples, this engagement may be sufficient to form an attachment between the barb 12 and the strut 14. A fixing element 24, such as a weld, may optionally be provided to further secure the barb 12 to the strut 14. In the event that the fixing element 24 weakens, or is otherwise compromised, the aperture 30 may retain the barb 12 and prevent the barb 12 from detaching from the strut 14. Further, external forces that may contribute to or cause breakage of the barb at a point of attachment to the stent 10 are transferred to the aperture, thus reducing the possibility of fracture at the point of attachment.

In the example shown in FIG. 1, the barb 12 is attached to the inner radial surface of the stent 10 via fixing element 24, the barb body 22 extends distally from the base 18 through the aperture 30, and the anchor 12 extends radially outwardly from the outer radial surface of the stent 10. When a force is applied to the anchor 20, a resulting stress will be transmitted towards and focused at the barb-stent junction 25 at the outer radial surface of the stent 10. Because the weld 24 is spaced apart from the barb-stent junction 25, unlike in the prior art where the weld is disposed at the barb-stent junction, the force will not be focused at the weld. Accordingly, the weld may be less susceptible to weakening during use.

The weld 24 may be spaced apart from the barb-stent junction 25 by a distance that is approximately equal to the distance between opposing openings of the aperture. Alternatively, the weld 24 may be spaced apart from the junction 25 by a greater distance. For example, the weld 24 may be disposed along the strut 14 and spaced from the aperture 30 along a longitudinal axis of the stent.

The aperture 30 has an inner dimension that may be equal to or greater than a corresponding outer dimension of the barb portion that is disposed within the aperture. In one example, the barb 12 may have a diameter of 0.020 inches, and the aperture 30 may have an inner diameter that is 0.020 inches or greater. In another example, the barb 12 may have a diameter of 0.010 inches, and the aperture 30 may have an inner diameter that is 0.010 inches or greater. In other examples, the aperture 30 may have an inner diameter that is less than or equal to 0.030 inches, less than or equal to 0.020 inches, or less than or equal to 0.010 inches.

As used herein, the term "diameter" refers generally to an inner or outer radial dimension of an aperture or barb, respectively. The use of the term is not limited to barbs and/or apertures having a circular cross-section and includes barbs and/or apertures having non-circular cross-sections (for example, elliptical and polygonal cross-sections).

The aperture 30 may have an inner contour that corresponds with or conforms to an outer contour of the barb 12. For example, the aperture 30 may have an inner diameter that is generally equal to, or not substantially greater than, an outer diameter of the barb 12. Accordingly, the barb 12 may frictionally and/or mechanically engage the stent 10 within the aperture 30. One advantage of this feature is that it may increase the area of surface contact between the stent 10 and the barb 12, and increase the bond between the stent and the barb. In some examples, the barb 12 may be attached to the stent 10 via a fixing element 24, such as a weld. In other examples, the engagement between the stent 10 and the barb 12 within the aperture 30 may be sufficient so that a fixing element is not necessary.

FIG. 2 depicts a stent 10 that comprises a plurality of barbs 12, each having an anchor 20 that extends outwardly at an oblique angle to the stent axis A. The barbs 12 may be retractable and have a retracted configuration and an extended configuration. In the extended configuration (shown in FIG. 2), the anchors 20 extend outwardly from the prosthesis at an angle that allows the anchors 20 to engage a surrounding vessel. For example, the anchors 20 may be disposed at an angle of about 20-50° with respect to the axis A. In the retracted configuration, the anchors 20 extend at an angle that limits or prevents the anchors from engaging a surrounding vessel. For example, the barbs 12 may be disposed at an angle of about 0-20° with respect to the axis A. As in FIG. 1, each of the barbs 12 may pass through the stent 10.

Figure 3D:
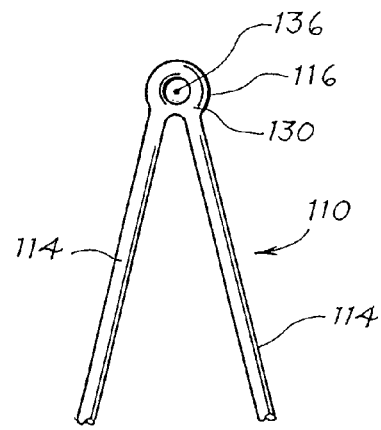

FIGS. 3A-3E depict additional exemplary stents 110. The stents 110 comprise at least two struts 114 joined by at least one apex 116. In each of the figures, an aperture 130 is shown and is formed in at least one of the struts 114. Each aperture 130 defines a cavity or passageway 136 having a length. In FIG. 3A, the aperture 130 is provided at a medial location along the length of the strut 114. The aperture 130 may be provided, for example, by drilling, machining, or otherwise removing material from the stent 110. Examples of such processes include laser drilling, electrochemical erosion, and electrical discharge machining ("EDM"). Alternatively, the aperture 130 could be bent, molded, or forged in the stent 110. Such an aperture 130 may occupy a volume and constitute a void within the strut 114, and accordingly, the size of the aperture 130 may be limited by the dimensions of the strut. In general, as the size of the aperture 130 increases in relation to the size of the strut 114, the stent may become weaker and more susceptible to wear. Accordingly, larger apertures 130 may be provided, simply by increasing the overall thickness of the strut 114.

As shown in FIG. 3B, a strut 114 may be provided having a generally uniform outer contour over a majority of its length and a region of increased thickness corresponding with the location of the aperture 130. Thus, in the example shown in FIG. 3B, the majority of the strut 114 may have a relatively low thickness so that the overall stiffness of the stent is not adversely affected. The aperture 130 may be provided, for example, by any of the means described above.

In FIG. 3C, an aperture 130 is provided and comprises a winding 134. The winding 134 may be provided, for example, by bending or plastically deforming the wire comprising the strut 114. FIG. 3D depicts an aperture 130 that is disposed at an apex 116 of the stent 110. The aperture 130 may be provided by any of the means previously described.

Figure 3E:
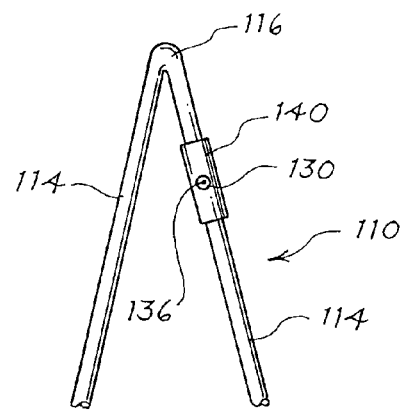

In FIG. 3E, the stent 110 comprises a plate 140 that is affixed to a strut 114. In one example, the strut 114 may comprise two wire ends and the plate 140 may comprise a cannula sleeve that covers the wire ends to form the strut 114. The plate 140 has an outer dimension that is generally greater than the corresponding outer dimension of the strut 114. The aperture 130 is formed in the plate 140. The aperture 130 may be provided by any of the means previously described.

Figures 4A, 4B, 4C:
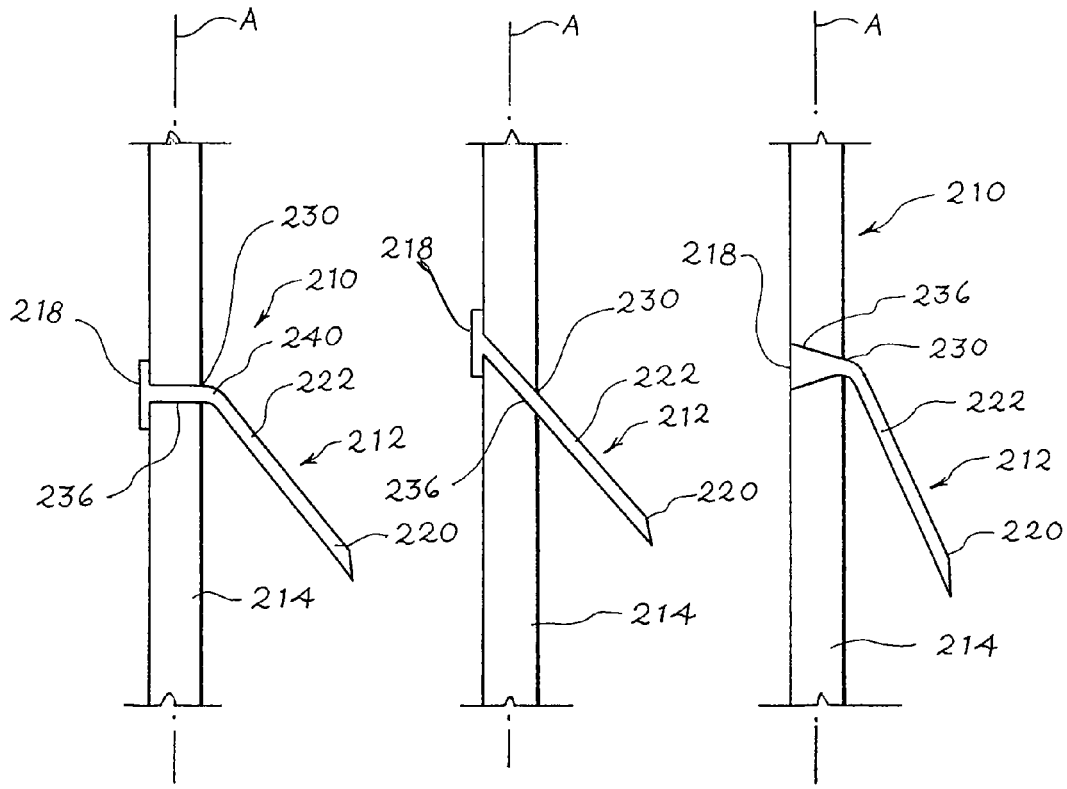
FIGS. 4A-4C are side schematic views of various intraluminal prostheses comprising a stent and a barb.

FIGS. 4A-4C illustrate additional exemplary stents, each comprising at least one strut 214 having an aperture 230. In each example, a barb 212 is provided and comprises a base 218, a distal anchor 220, and a barb body 222 extending therebetween. At least a portion of the barb 212 is disposed within the aperture 230 and at least the anchor 220 extends from the aperture 230 and away from the strut 214.

In FIG. 4A, the aperture 230 forms a passageway or cavity 236 that extends through the strut 214 at a generally transverse angle with respect to the axis A of the strut 214. The portion of the barb 212 that is disposed within the cavity 230 has an outer contour that corresponds with the contour of the cavity 236. For example, the barb 212 may have a diameter that is equal to or slightly smaller than the diameter of the cavity 236. The barb base 218 may have a diameter that is larger than the diameter of the cavity 236. This may prevent the base 218 from sliding distally through the aperture 230 and may increase the total area of surface contact between the stent 210 and the barb 212. The barb 212 may be further secured to the strut 214, for example, by a weld (not shown). The anchor 220 extends distally from the stent 210 at an oblique angle with respect to the axis A of the strut 214. Accordingly, a bend 240 may be provided in the barb body 222 to orient the anchor 220 at the oblique angle.

In FIG. 4B, the strut 214 comprises an aperture 230 having a cavity 236 that extends through the stent at a generally oblique angle with respect to the axis A of the strut 214. A barb 212 is provided and passes through the aperture 230. The barb 212 may have an outer contour that corresponds with the inner contour of the cavity 236, as described above. The anchor 220 extends distally from the stent 210 at an oblique angle with respect to the strut axis A. In the example shown in FIG. 4B, the cavity 236 is aligned so that a bend may not be required to properly orient the anchor 220.

In the examples depicted in FIGS. 4A and 4B, the aperture 230 comprises a cavity 236 with a generally cylindrical inner contour. In other examples, the cavity 236 may have a non-cylindrical inner contour. For example, in FIG. 4C, the cavity 230 comprises a generally frustoconical inner contour.

The cavity 236 may have an inner contour that conforms to an outer contour of the barb 212 at a point of engagement. For example, in FIG. 4C, the cavity 236 conforms to a generally frustoconical outer contour of the barb 212. In this example, the barb base 218 has a diameter that is less than, or equal to, the corresponding diameter of the cavity 236. When the barb 212 is placed within the aperture 220, the frustoconical base 218 may engage the frustoconical cavity 236 to limit movement between the barb 212 and the stent 210. The frustoconical contours provide a greater area of surface contact than a cylindrical contour, thus increasing the integrity and strength of the attachment between the stent 210 and the barb 212.

Figure 5A:
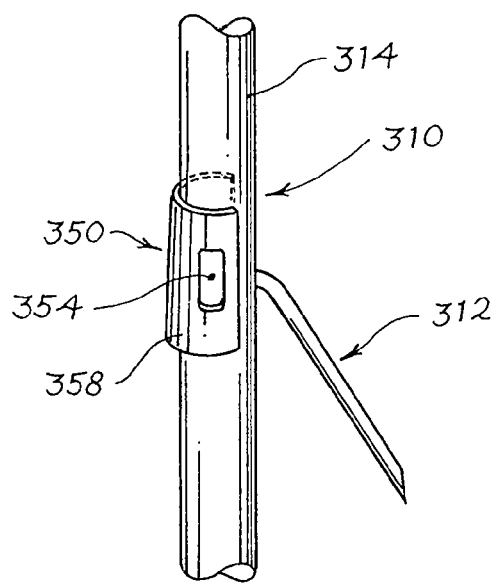
FIGS. 5A and 5B are side and front perspective views, respectively, of another intraluminal prosthesis comprising a stent and a barb.
Figure 5B:
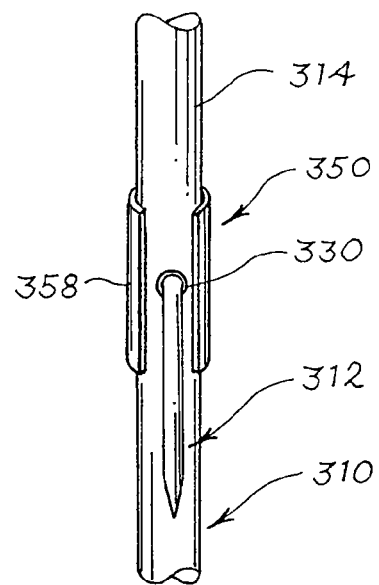

FIGS. 5A and 5B depict another exemplary intraluminal prosthesis. A stent 310 comprises at least one strut 314 and a barb 312 passing through an aperture 330 in the strut 314. At least a portion of the barb 312 is disposed within the aperture 330 and at least the anchor (not shown) extends from the aperture 330 and away from the strut 314.

In these examples, an attachment structure 350 is provided for attaching the barb 312 to the strut 314. As shown in FIGS. 5A and 5B, the attachment structure 350 may comprise a cannula 358 that extends at least partially about the strut 314. The cannula 358 may extend more than 90° about the strut 314 so that the attachment structure 350 may attach to the strut 314 by crimping or "snapping" the cannula 358 to the strut. In some examples, this attachment may be sufficient such that a fixing element, such as a weld, may not be necessary. In other examples, a fixing element (not shown) may be provided in addition to the attachment structure 350. The cannula 358 may comprise one or more fenestrations 354 for providing an increased bonding area for gluing, soldering, or welding the cannula 358 to the strut 314. In some examples, the cannula 358 may comprise a winding, such as a barb winding, that extends at least partially about the strut 314.

The attachment structure 350 may be integrally formed with the barb 312. In these examples, the barb 312 and the attachment structure 350 may comprise a unitary or monolithic structure. In other examples, the attachment structure 350 may be provided as a separate structure from the barb 312. For example, a stent 210 and a barb 212 may be provided, as shown in FIGS. 4A-4C. After the barb 212 is placed within the aperture 230 and the barb base 218 is seated, a separate cannula 358 may be provided and crimped, snapped, or otherwise secured over the strut 214 to constrain the base 218. As described above, the engagement between the barb 212 and the aperture 230 prevents the barb from sliding distally through the passageway 236. Further, the attachment structure 350 may prevent the barb 212 from sliding proximally through the passageway 236. Thus, the barb 212 may attach to the stent 210 without placing a weld or other such bond between the barb and the stent. The cannula 358 may optionally be welded to the strut 214 to increase the attachment between the cannula 358 and the stent 210, and to prevent detachment therebetween.

Figure 6:
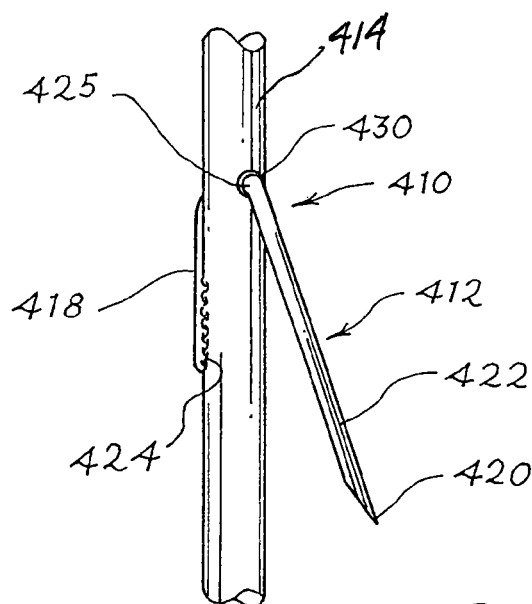
FIG. 6 is a side perspective view of another intraluminal prosthesis comprising a stent and a barb.

FIG. 6 depicts another exemplary intraluminal prosthesis that comprises a stent 410 and a barb 412. The barb 412 passes through an aperture 430 in a strut 414. The barb base 418 may be attached to the strut 414 by a fixing element 424, such as a weld. Alternatively, or additionally, an attachment structure (not shown) may be provided for attaching the barb 412 to the strut 414. The barb body 422 extends distally from the base 418 towards the aperture 430 and distally from the aperture 430 towards the anchor 420 and away from the strut 414. In the example shown in FIG. 6, the base 418 and the weld 424 are spaced apart from the aperture 430, thus increasing the distance between the weld and the high-stress barb-stent junction 425. Accordingly, in use, any stress on the anchor 420 will be transmitted to and focused at a region of the prosthesis that is spaced apart from the weld 424.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A stent comprising:
   a plurality of elongate struts each having a first end and a second end;
   an aperture formed in at least one of the plurality of struts; and
   a barb having a base and a distal anchor;
   where the barb base is attached to the at least one of the plurality of elongate struts and the barb extends distally from the base through the aperture;
   where the at least one of the plurality of elongate struts has a longitudinal axis and the barb extends from the at least one of the plurality of elongate struts at an oblique angle to the longitudinal axis
   and
   where the barb frictionally engages the stent within the aperture.

2. The stent of claim 1, where the aperture is formed in an end of the strut.

3. The stent of claim 1, where the aperture is formed between the first and second ends of the at least one of the plurality of elongate struts.

4. The stent of claim 1, wherein the plurality of elongate structs a first strut and a second strut joined at an apex, where the aperture is formed in the apex.

5. The stent of claim 1, where the aperture comprises a winding.

6. The stent of claim 1, where the aperture is forged in the at least one of the plurality of elongate struts.

7. The stent of claim 1, where the aperture defines a generally cylindrical cavity.

8. The stent of claim 1, where the aperture defines a generally frustoconical cavity.

9. The stent of claim 1, where the barb base has a diameter that is greater than a diameter of the aperture.

10. The stent of claim 1, where aperture defines a cavity that extends at an oblique angle with respect to a longitudinal axis of the strut.

11. The stent of claim 1, where the aperture defines a cavity that extends at a generally transverse angle with respect to a longitudinal axis of the strut.

12. The stent of claim 1, where the aperture has an inner diameter that is less than or equal to 0.030 inches.

13. The stent of claim 12, where the aperture has an inner diameter that is less than or equal to 0.020 inches.

14. The stent of claim 13, where the aperture has an inner diameter that is less than or equal to 0.010 inches.

15. The stent of claim 1, where the barb base is spaced apart from the aperture along the at least one of the plurality of elongate struts.

16. The stent of claim 1, where the barb base is disposed at least partially within the aperture.

17. The stent of claim 1, where the barb base is disposed adjacent the aperture.

18. The stent of claim 1, further comprising a means for preventing the barb from sliding within the aperture.

19. The stent of claim 1, further comprising any two or more of the following:
   the aperture is formed in an end of the strut;
   the aperture is formed between the first and second ends of the strut;
   a first strut and a second strut of the plurality of elongate struts joined at an apex, where the aperture is formed in the apex;
   the aperture comprises a winding;
   the aperture is forged in the at least one of the plurality of elongate struts;
   the aperture defines a generally cylindrical cavity;
   the aperture defines a generally frustoconical cavity;
   the barb base has a diameter that is greater than a diameter of the aperture;
   the aperture defines a cavity that extends at an oblique angle with respect to a longitudinal axis of the at least one of the plurality of elongate struts;

the aperture defines a cavity that extends at a generally transverse angle with respect to a longitudinal axis of the at least one of the plurality of elongate struts;

the aperture has an inner diameter that is less than or equal to 0.030 inches, 0.020 inches, or 0.010 inches;

the barb base is spaced apart from the aperture along the at least one of the plurality of elongate struts;

the barb base is disposed at least partially within the aperture;

the barb base is disposed adjacent the aperture; and a means for preventing the barb from sliding within the aperture.

20. A stent comprising a plurality of elongate struts each having a first end and a second end, and a barb having a base and a distal anchor, where the barb base is attached to at least one of the plurality of elongate struts and the barb extends distally from the base and passes through the at least one of the plurality of elongate struts and extends from the at least one of the plurality of elongate struts at an oblique angle to a longitudinal axis of the at least one of the plurality of struts.

21. The stent of claim 1, where the aperture has an inner contour that conforms to an outer contour of the barb.

22. The stent of claim 1, where the barb mechanically engages the stent within the aperture.

23. The stent of claim 1, where the aperture has an inner diameter that is generally equal to an outer diameter of the barb.

24. A stent comprising:

an elongate strut having a first end, a second end and a longitudinal axis;

an aperture formed in the strut; and a barb having a base and a distal anchor;

where the barb base is attached to the strut and the barb extends distally from the base through the aperture; and where the aperture has an inner diameter that is generally equal to a corresponding outer diameter of the barb portion that is disposed within the aperture, and wherein the distal anchor extends from the strut at an oblique angle to the longitudinal axis.

25. The stent of claim 24, where the aperture has an inner contour that conforms to an outer contour of the barb.

26. The stent of claim 24, where the barb frictionally engages the stent within the aperture.

27. The stent of claim 24, where the barb mechanically engages the stent within the aperture.

\* \* \* \* \*